United States Patent [19]
Winstanley et al.

[11] Patent Number: 5,223,165
[45] Date of Patent: Jun. 29, 1993

[54] USE OF ALKYL GLYCOSIDES FOR DUST SUPPRESSION

[75] Inventors: Richard A. Winstanley; Michael W. Swartzlander, both of Forsyth, Ill.; Thomas W. Cooke, Greensboro, N.C.

[73] Assignee: Henkel Kommanditgesellschaft auf Aktien, Duesseldorf

[21] Appl. No.: 965,987

[22] Filed: Oct. 22, 1992

Related U.S. Application Data

[63] Continuation of Ser. No. 433,468, Nov. 9, 1989, abandoned, which is a continuation of Ser. No. 200,804, May 31, 1988, abandoned.

[51] Int. Cl.$^5$ ............................................. C09K 3/22
[52] U.S. Cl. ............................. 252/88; 252/174.17; 44/577; 44/602
[58] Field of Search ............... 252/88, 174.17; 44/577, 44/602

[56] References Cited

U.S. PATENT DOCUMENTS

| | | | |
|---|---|---|---|
| 3,219,656 | 11/1965 | Boettner | 260/210 |
| 3,547,828 | 12/1971 | Mansfield | 252/351 |
| 3,640,998 | 2/1972 | Mansfield | 260/210 |
| 3,974,138 | 8/1976 | Lew | 536/4 |
| 4,136,050 | 1/1979 | Brehm | 252/252 |
| 4,169,170 | 9/1979 | Doeksen | 427/427 |
| 4,171,276 | 10/1979 | Brehm | 252/252 |
| 4,369,121 | 1/1983 | Callahan et al. | 252/252 |
| 4,400,220 | 8/1983 | Cole | 134/18 |
| 4,425,252 | 1/1984 | Cargle et al. | 252/88 |
| 4,428,984 | 1/1984 | Shimizu et al. | 427/220 |
| 4,472,170 | 9/1984 | Hellyer | 44/51 |
| 4,487,615 | 12/1984 | Taylor et al. | 55/84 |
| 4,557,729 | 12/1985 | McDaniel et al. | 8/111 |
| 4,582,511 | 4/1986 | Siddoway et al. | 44/6 |
| 4,594,268 | 6/1986 | Kirwin | 427/136 |
| 4,597,770 | 7/1986 | Forand et al. | 44/51 |
| 4,627,931 | 12/1986 | Malik | 252/174.21 |
| 4,678,595 | 7/1987 | Malik et al. | 252/174.17 |
| 4,701,331 | 10/1987 | Grabitz | 426/302 |
| 4,737,305 | 4/1988 | Dohner | 252/88 |
| 4,801,635 | 1/1989 | Zinkan et al. | 524/156 |
| 4,834,903 | 5/1989 | Roth et al. | 252/174.17 |

FOREIGN PATENT DOCUMENTS 132043 1/1985 European Pat. Off.
195638 9/1986 European Pat. Off.

OTHER PUBLICATIONS

R. W. Shaw, "Air Pollution By Particles", *Scientific American*, 256:96-103 (Aug. 1987).
Tacky, The American College Dictionary, p. 1233, Random House Inc., New York, 1970.
M. O. Kestner, "How To Control Fugitive Dust Emissions From Coal-Fired Plants", *Power*, pp. 43-49 (Jun. 1987).
W. B. Membrey, "Suppression of Dust During Coal Handling", *Proceedings of Second Australian Coal Preparation Conference: Total Recovery of the Energy Resource*, pp. 38-60, Coal Preparation Society of New South Wales (1983).
K. D. Rosbury and R. A. Zimmer, "Cost-Effectiveness of Dust Depressants on Surface Coal Mine Haul Roads", p. 1, 7th Annual Meeting of Air Pollution Control Association (Jun. 1983).

(List continued on next page.)

*Primary Examiner*—Hoa Van Le
*Attorney, Agent, or Firm*—Ernest G. Szoke; Wayne C. Jaeschke; Daniel S. Ortiz

[57] ABSTRACT

A method of suppressing the generation or persistence of dust is provided. An aqueous composition of a higher alkyl glycoside is placed in contact with a friable solid material (e.g. coal) to suppress the generation of dust therefrom. The alkyl glycoside is generally present in the aqueous composition at a level of from about 0.001% by weight to about 1% by weight of the aqueous composition. Because of the nature of this particular use, highly colored compositions can be employed in the method. A composition used as a dust suppressant comprised of a higher alkyl glycoside and a hydrophilic binder material is also provided.

8 Claims, No Drawings

OTHER PUBLICATIONS

H. W. Cole, "Foam Suppressants for Control of Dust", *Coal Mining and Processing,* vol. 14, pp. 98-104 (1977).

D. V. Diep and M. Y. Corpuz, "Dust Control in Industrial Power Plants", 1987 Purdue Industrial Fuel Conference, Sep. 30 and Oct. 1, 1987 (Nalco Chemical Co. 1987).

S. Chander, et al., "Wetting Behavior of Coal in the Presence of Some Nonionic Surfactants", *Colloids and Surfaces,* vol. 26, pp. 205-216 (1987).

I. O. Salyer, et al., "Foam Suppression of Respirable Coal Dust", Natl. Tech. Info. Serv., Abstract No. USGPB82-166505 (Dec. 1970).

I. O. Salyer, et al., "Foam Suppression of Respirable Coal Dust", Natl. Tech. Info. Serv., Abstract No. USGPB-204522.

J. H. Meyer, et al., "Rotary Rail Car Dumper Coal Dust Depressant Experiment", Natl. Tech. Info. Serv. Abstract No. USGPB85-135689/XAB.

MSDS for DUSTRACT from Midwest Industrial Supply Co. Nov. 15, 1985.

MSDS for SOIL-SEMENT from Midwest Industrial Supply Co.

MSDS for DUST-BAN 7981 from Nalco Chemical Co.

MSDS for DCL-1870 from Calgon Corporation.

MSDS for DCL-1817 from Calgon Corporation.

USE OF ALKYL GLYCOSIDES FOR DUST SUPPRESSION

This application is a continuation of application Ser. No. 07/433,468 filed on Nov. 9, 1989, now abandoned, which is a continuation of Ser. No. 07/200,804 filed on May 31, 1988, now abandoned.

FIELD OF THE INVENTION

This invention relates to methods of dust suppression and to compositions useful in dust suppression.

BACKGROUND OF THE INVENTION

To reduce air pollution from airborne dust, cf. R. W. Shaw, "Air Pollution by Particles", Scientific American, 257:96-103 (August 1987), in many environments which contain or are in the vicinity of loose aggregate material, e.g. mining and industrial locations which produce or use coke, coal, sand or other loose aggregate material, one must provide means for preventing dust particles from accumulating in the surrounding environment. For example, in coal mines it is often mandatory to provide means for preventing accumulations of coal dust from remaining suspended in the air.

Various dust suppressant compositions and methods are known in the art for spraying in air to reduce airborne dust or for spraying on substances which develop dust, for example coal aggregates. U.S. Pat. No. 4,369,121 (Callahan et al) discloses a composition for controlling dust which comprises a cellulose ether and a wetting agent such as an ethylene oxide condensate of nonyl- or octylphenol, ethylene oxide condensates of straight chain alcohol, fatty acid amides, quaternary ammonium compounds, organic phosphate esters, and sulfonic acids. U.S. Pat. No. 4,169,170 (Doeksen) discloses a composition and method for controlling dust during coal transportation wherein the composition comprises an aqueous solution containing an asphalt emulsion or a black liquor lignin product and a water soluble ethoxylated alkyl phenol. U.S. Pat. No. 4,425,252 (Cargle et al) discloses an aqueous coal dust abatement composition including a water soluble sulfonic acid salt and ethoxylated nonyl phenol and U.S. Pat. No. 4,428,984 (Shimizu et al) discloses a method of preventing dusts by spreading an aqueous solution including an ethoxylated alkyl phenol, alcohol, fatty acid, amine or fatty acid amide and a polyhydric alcohol.

U.S. Pat. No. 4,487,615 (Taylor et al) discloses a method of reducing mine dust by spraying water including a surfactant produced by reacting ethylene oxide with linear primary alcohols. U.S. Pat. Nos. 4,136,050 (Brehm) and 4,171,276 (Brehm) disclose a dust suppression composition comprising an aqueous solution of alkylphenoxy polyethoxy ethanol and a copolymer of ethylene oxide and propylene oxide.

U.S. Pat. No. 4,737,305 (Dohner) disclose a dust suppressant composition comprising an aqueous solution of a dust suppressant comprising an ethoxylated alcohol and an ethoxylated alkyl phenol. The patent also discloses methods of suppressing dust by spraying such compositions in dusty air or applying the composition to a dust generating substance.

However, the above dust suppressing compositions and methods all have various disadvantages in that the compositions are not immediately effective (and require an extended time for satisfactory performance) and/or are not sufficiently persistent in suppressing dust or that the compositions include excessive aromatic or other less biodegradable or toxic materials. There is therefore a need for an efficient dust suppressant composition which enhances the settling and/or suppresses the generation of air-borne dust and which is substantially biodegradable and nontoxic in the environment.

SUMMARY OF THE INVENTION

In one aspect, this invention relates to a method of suppressing dust comprising contacting a particulate friable solid in a substantially dry environment with an aqueous composition comprised of a higher alkyl glycoside composition. By "higher alkyl glycoside" is meant a glycoside having an alkyl substituent that averages more than 4 carbon atoms in size.

In another aspect, this invention also relates to a dust suppressant composition comprising a mixture comprised of:

(a) a higher alkyl glycoside composition, and
(b) a hydrophilic binder material.

The composition can exist in many forms, i.e. as a concentrate, as a dilute aqueous solution and/or dispersion, and as a finely divided fluid form (e.g. a mist) thereof. By "hydrophilic binder material" is meant a water soluble or dispersible material that can contribute to the tackiness of the composition in the environment.

DETAILED DESCRIPTION OF THE INVENTION

The method of this invention relates to the suppression of dust from a particulate, friable solid. By "dust" is meant any particulate solid material that is susceptible to suspension in air or other atmospheric environment. Accordingly, the term dust includes particles having an average diameter of up to 1 cm (though typically only up to about 300 micron) and down into the fume range (e.g. typically as low as 0.001 micrometers). The particulate friable solid will be in a substantially dry, non-fluid environment, e.g. the solid will be comprised of less than about 15% by weight water. The friable solids can have a varying chemical composition. Examples include organic materials e.g. sawdust, grain dust, fiber dust, or animal waste, and mineral particles, especial silicic or carbonaceous minerals, e.g. coal dust, soil dust (humus and/or subsoil), gravel dust, fine clay, lime dust, fly ash, and the like.

The method of this invention employs an aqueous composition comprised of a higher alkyl glycoside. Compositions comprised of higher alkyl glycosides are known materials possessing surfactant properties. An "alkyl glycoside" as used herein means a material which contains 1 or more units of a sugar source such as glucose and a hydrophobic organic tail. If the glycoside contains glucose units, then it is referred to as a glucoside. If the glycoside contains 2 or more units of glucose, e.g. a polymer, then the material is referred to as a polyglucoside. If the glycoside contains 2 units of glucose, e.g. a polymer, then the material is referred to as a glycoside or a polyglycoside having a degree of polymerization (D.P.) of 2. If the glycoside is an alkyl glycoside then the material is substituted in the one position with an alkoxyl moiety rather than the $C_1$ hydroxyl of the starting sugar. Therefore, the attachment of the alkoxyl moiety is by an acetal linkage to the sugar.

The term polyglycoside refers to a D.P. 2 and higher material. It is also to be noted herein that the D.P. value is stated as an average insofar as a mixture of glycosides will be obtained. That is, when starting with polysaccharides, it would be expected that D.P. 1 through higher materials, e.g. D.P. 5, 10, 20, etc. would be obtained. It has also been observed, however, that higher D.P. products will be obtained even when using as the sole saccharide source a material such as dextrose which is a monomer. Accordingly, the products obtained result not only from acetal formation but also from polymerization. Similarly, some of the higher D.P. materials may be hydrolyzed in processing to give lower D.P. glycosides. Preferably, the D.P. of the glycosides herein is from 1.0 to 15, preferably 1.2 to 3 when a polyglycoside is the product. The preferred glycoside herein is a glucoside. The term glycoside also embraces derivatives of glycosides such as the alkylene oxide adducts of Mansfield (U.S. Pat. No. 3,640,998 issued Feb. 8, 1972).

The alkyl glycoside composition can be made by any number of methods known to those skilled in that art. For example, it has been suggested by Boettner in U.S. Pat. No. 3,219,656 issued Nov. 23, 1965 that an acid catalyzed route for obtaining an alkyl polyglycoside may be utilized starting with a saturated alcohol and dextrose. Similarly, Mansfield in U.S. Pat. No. 3,547,828 issued Dec. 15, 1970 teaches a method of obtaining glycosides.

U.S. Pat. No. 3,974,138 issued to Lew on Aug. 10, 1976 states that it is preferable to use glucose as a starting material for the preparation of butyl polyglycoside. It has been observed, according to Lew, that it is extremely difficult when starting with the sugar source to obtain higher alkyl polyglycosides directly. That is, the starting sugar materials are highly water-soluble whereas dodecyl alcohol (to add a $C_{12}$ group is extremely water-insoluble. Therefore, the route proposed by Lew is to form an intermediate butyl glycoside and to thereafter transetherify to obtain the higher alkyl polyglycosides. Other publications which disclose the preparation of alkyl glycosides include E.P.O. Publication No. 132,043 (Davis et al.).

It is also known that the methods most commonly employed to produce alkyl glycosides often generate highly colored by-products whose formation is difficult to efficiently prevent and which are not easily susceptible to efficient removal or decolorization. See, for example, the disclosure of U.S. Pat. No. 4,557,729 (McDaniel et al.). It is an advantage of this invention that highly colored alkyl glycosides can be efficiently used in a beneficial manner by suppressing dust generation.

The alkyl glycoside is typically present in the aqueous composition contacted with the dust generating material at a level of from about 0.001% to about 1.0% by weight of the aqueous composition, more typically from about 0.01% to about 0.1%. The amount of aqueous composition used to contact the particulate, friable solid, can vary, but will generally be such that the particulate friable solid will remain, or shortly return to, a substantially dry, non-fluid state. The aqueous composition can be constituted of water from most any environmentally acceptable source (e.g. tap water, lake water, river water, well water, waste water, etc.). The composition is preferably made by adding the alkyl glycoside to water rather than the reverse for good dispersibility of the glycoside. The aqueous composition may also include other functional additives, e.g. diluents such as glycols and other alcohols, freezing point depressants such as, aromatic sulfonates, mineral salts (NaCl, KCl, etc.) and/or urea, auxiliary surfactants such as nonyl phenol ethoxylates, dialkyl sulfosuccinates, and/or lignin sulfonates.

The aqueous composition also preferably contains a hydrophilic binder material, as noted above. Such materials can come from a variety of sources, but preferred sources can be generally divided into two groups, i.e. (i) synthetic polymeric materials and (ii) carbohydrate-based materials. Examples in the former group include acrylic latexes, polyvinyl alcohol, and other addition or condensation polymers and/or oligomers having sufficient hydrophilic character to be soluble and/or dispersible in the aqueous composition. Examples in the latter group include polysaccharide materials, e.g. starch, starch derivatives, cellulose derivatives, natural gums, and/or polydextrose (e.g. as a by-product of alkyl glycoside formation), and monosaccharides (e.g. dextrose, methyl glucoside, and the like) as well as simple or complex mixtures comprised of these (e.g. dextrose greens (mother liquor from dextrose crystallization) corn syrups (as syrups or dried solids), corn steep liquor (a by-product of corn wet milling) and the like). Because the color of the aqueous composition or a concentrate used to prepare the composition is unlikely to be of concern, off-specification materials can typically be used as hydrophilic binder materials.

Because it is often inefficient to transport water, the alkyl glycoside composition and hydrophilic binder will often be formulated as concentrates, e.g. at least 10% active solids, (together or as separate components) for dilution with water to make an aqueous dust suppressant composition at or near the site of use.

The aqueous composition can be placed in contact with the friable solid material in any manner effective to suppress the generation of dust therefrom. For example, the composition can be sprayed on a friable solid prior to or even during activity i.e. the imposition of mechanical stress (e.g. compaction, shearing, grinding, grading, shoveling, and the like) which causes the generation of dust from the solid. The aqueous composition can also be atomized (i.e. misted) into a atmosphere comprised of a finely divided solid to both aid in precipitation or settling of the solid and in minimizing regeneration of dust from the precipitate.

EXAMPLES

I. Experimental

To investigate the dust suppressant properties of alkyl glycosides, two separate and distinct alkyl glycosides, comprised of compounds of the formula $CH_3-(CH_2)_n-Glucose_x$ were used in the following experiments, as well as a blend of these:

TABLE 1

| ALKYL GLYCOSIDE | DESCRIPTION |
| --- | --- |
| AG1 | n = 9 average, x = 1.5 avg. |
| AG2 | n = 11.5 avg., x = 1.8 avg. |
| AG3 | 50/50 wt. blend of AG1 and AG2 |

These alkyl glycosides were evaluated in the following tests against other materials as described below:

TABLE 2

| ABBREV. | SUPPLIER; PRODUCT | COMPOSITION | ACTIVES CONTENT | RECOMMENDED APPLICATION RATE |
|---|---|---|---|---|
| X1 | Johnson-March MR 20/40 | nonyl phenol ethoxylate, dioctyl sodium sulfosuccinate, butyl cellosolve | ~49% (60% volatile) | dilute to ~1:3500 with water |
| X2 | Nalco; Dust-Ban 7981 | "a blend of ligno-sulfonate and a polyglycol ester in mineral seal oil and fuel" | 63% solids found | dilue 1:3 with water; apply 0.25-1.5 gal. of diluted product per sq. yd. |
| X3 | Midwest Industrial Supply; "Dustract" | sodium dihexyl sulfosuccinate, sodium dioctyl sulfosuccinate, butoxyethanol | 11.5% solids found | dilute 1:2000 with water (or 0.05% as is, ~0.006% solids) |
| X4 | Midwest Industrial Supply; "Soil-Sement" | "aqueous acrylic emulsion" "a binding and cohesive concentrate" (bulletin) | 50% solids found | dilute 1:9 with water then 1 gal. dilution per 50-100 ft.$^2$ (5.5 to 11 yd$^2$) (~8.34 lbs. at 5% actives per 5.5-11 yd.$^2$) (~0.04-0.08 lbs. actives/yd.$^2$) |
| X5 | Union Carbide Corp. Tergitol TM NP-9 | nonylphenol ethoxylate (9 mol EO) | — | — |
| X6 | MacKanate DOS-75 | Dioctyl sodium Sulfosuccinate | — | — |
| X7 | Horizon Chemical Div. Staley Continental Inc. Sta-meg TM 101 | Methyl Glucoside | — | — |
| X8 | Mother liquor from the commercial crystallization of dextorse, commonly referred to as "dextrose greens" | | | |
| X9 | The liquid steep water left after the steeping of corn as part of the commercial wet milling thereof | | | |

A. Coal Dust Sinking Time-Wetting

In this experiment, solutions of the various surfactants (and commercial products) were made in a range of concentrations, and the resulting solutions were placed in a 500 ml graduated cylinder. Then 0.25 g of pulverized coal dust (fine enough to go through a 48 mesh sieve) were carefully laid on top of the surface of the solutions. The time was recorded at which >90% of the dust had wetted and begun to sink.

The following materials were tested in this manner in distilled water (see Table A1) and in 300 ppm hard water (3Ca/2 Mg) (see Table A2): AG1, AG2, AG3, X1, X3, X5, and X6.

The following materials were also tested in 200 ppm hard water (see Table A3): AG2, AG3, X1, X3, and X5.

TABLE A1

| | Sinking Time of Coal Dust in Distilled Water | | | | | | |
|---|---|---|---|---|---|---|---|
| Concentration | Time (Sec) | | | | | | |
| (Wt % Actives) | AG1 | AG2 | AG3 | X1 | X3 | X5 | X6 |
| 0.1 | 13.6 | 9.9 | 17.4 | 28 | 43.1 | 9.4 | 21 |
| 0.05 | 28.4 | 14.8 | 23 | 66 | 161 | 11.4 | 97 |
| 0.025 | 63 | 23.4 | 46 | 174 | 3,600 | 20.4 | 237 |
| 0.01 | 311 | 64 | 165 | 2160 | * | 63 | 3,600 |
| 0.005 | 3,600 | 401 | 349 | * | * | 153 | * |
| 0.0025 | * | 546 | 2,400 | * | * | 702 | * |
| 0.00125 | * | 3,000 | * | * | * | 3,060 | * |

TABLE A2

| | Sinking Time of Coal Dust in 300 pm Hard Water | | | | | | |
|---|---|---|---|---|---|---|---|
| Concentration | Time (Sec) | | | | | | |
| (Wt % Actives) | AG1 | AG2 | AG3 | X1 | X3 | X5 | X6 |
| 0.1 | 14.2 | 10.8 | 14 | 11.4 | 12.4 | 9.1 | 6 |
| 0.05 | 31.7 | 12.6 | 37 | 24 | 16.4 | 10.7 | 7.2 |
| 0.025 | 207 | 37.1 | 156 | 43.5 | 28.4 | 19.3 | 9.3 |
| 0.01 | 502 | 75 | 202 | 354 | 3,600 | 43 | 40.1 |
| 0.005 | 3,000 | 409 | 3,600 | 513 | * | 128 | 3,600 |
| 0.0025 | * | 613 | * | 1872 | * | 238 | * |
| 0.00125 | * | 3,000 | * | * | * | 2340 | * |

TABLE A3

| Sinking Time of Coal Dust in 2000 pm Hard Water | | | | | |
|---|---|---|---|---|---|
| Concentration | Time (Sec) | | | | |
| (Wt % Actives) | AG2 | AG3 | X1 | X3 | X5 |
| 0.1 | 31.9 | 17.4 | 22.2 | 6.1 | 16.5 |
| 0.05 | 99 | 60 | 46 | 7 | 20 |
| 0.01 | 63 | 230 | 969 | 63 | 180 |

B. Coal Dust Re-Wetting

In this experiment, 5.0 g of pulverized coal dust (48 mesh) were treated with 1.0 ml of the surfactant solutions at various concentrations, so that the resulting coal dust (when dried in a 110° C. oven) had a range of surfactant levels coated on the material. In a manner similar to the sinking time above, the treated coal dust (0.25 g) was carefully laid on the surface of distilled water in a graduated cylinder. Again, the time was measured for at least 90% of the dust to sink.

The following materials were tested by this method (See Table B): distilled water (to treat the coal), AG2, AG3, X1, X3, X5, and X6.

TABLE B

| Concentration | Coal Dust Rewetting Time | | | | | |
|---|---|---|---|---|---|---|
| | Time (Sec) | | | | | |
| (Wt % Active) | AG2 | AG3 | X1 | X3 | X5 | X6 |
| 1 | 5.4 | 9.3 | 10.8 | 16 | 4.7 | 19 |
| 0.5 | 12.8 | 32.6 | 48 | 134 | 13.6 | 88 |
| 0.1 | 20.5 | 53 | 0 | 360 | 16.9 | 30.0 |
| 0.05 | 45 | 300 | — | — | 30 | — |

C. Hygroscopicity (Moisture Pick-up) of Dried Solids

For this test, samples of the various surfactants were dried to solids. Then several grams of each were placed in aluminum weighing dishes and allowed to stand at ambient conditions for several weeks. The samples were periodically weighed to see if they picked up moisture from the atmosphere.

The following samples were tested (see Table C): AG1, AG2, X1, X2, X3, X5, and a blend of AG2 and X7 at 1:2.5 by wt., respectively.

TABLE C

| Hygroscopicity of Dried Solids | | | | | | | |
|---|---|---|---|---|---|---|---|
| Wt % in Excess of Original Weight | | | | | | | |
| Days | AG1 | AG2 | X1 | X2 | X3 | X5 | X7 | Blend of AG2 & X7 |
| 1 | 0 | 0 | 0 | 0 | 0 | 0 | 0 | 0 |
| 2 | 0.6 | — | 1 | 6 | 0.45 | 0 | — | — |
| 3 | — | — | — | — | — | — | — | 1.03 |
| 4 | — | — | — | — | — | — | — | — |
| 5 | 1.9 | 2.7 | 0.3 | 5.6 | 1.8 | −1 | 1.2 | 3.73 |
| 6 | — | — | — | — | — | — | — | — |
| 7 | — | — | — | — | 1.8 | — | 4.1 | 3.85 |
| 8 | — | — | — | — | — | — | — | — |
| 9 | 3.1 | 4 | −2.1 | 3.8 | 1.8 | −1.3 | 4.43 | 3.95 |
| 10 | — | — | — | — | — | — | — | — |
| 11 | — | 4.1 | −2.4 | 3.1 | 1.8 | −1.1 | 4.46 | 3.96 |

D. Blower ("Poofer") Test-Retardation of Drying

In this method, 15.0 g of pulverized coal dust (48 mesh) were treated with 3.0 g of surfactant solutions at 1.0% actives (for 0.2% on coal). This wet coal dust was placed in a glass cylinder (60 cm high, by 5.0 cm inside diam.). At several time intervals, compressed air was blown into the cylinder through the bottom at ~57 L/min. (setting 60, Cole-Palmer flow meter J-3216-40) for periods of 30 seconds each. (Note: The wet dust sat on a fine-mesh wire screen at the bottom end of the cylinder. An air baffle-plate under the screen prevented the air from blowing a hole through the middle of the dust.) A 70 mm × 20 mm glass vial is suspended in the cylinder by wire, with the bottom of the vial 20 mm above the wire screen. The empty vial is weighed. After each blast of compressed air (which blows up more and more dust as it dries), the vial is weighed again to determine the amount of dust settled into it.

The following materials and systems were evaluated (see Table D). Water only (Control), AG2, AG3, X1, X2, X3, X4, X6 and three separate blends of AG2 with X7, X8 or X9, at a 1:2.5 ratio by wt., respectively.

TABLE D

| | Retardation of Drying Dust Collected (gms) | | | | | | | | | | |
|---|---|---|---|---|---|---|---|---|---|---|---|
| | | | | | | | | | Blend of | | |
| Hours | Control | AG2 | AG3 | X1 | X2 | X3 | X4 | X6 | AG2 & X7 | AG2 & X8 | AG2 & X9 |
| 0 | 0 | 0 | 0 | 0 | 0 | 0 | 0 | 0 | 0 | 0 | 0 |
| 1 | 0.07 | 0.002 | 0 | 0 | 0 | 0 | 0.06 | 0.02 | 0 | 0.003 | 0.02 |
| 2 | 0.2 | 0.003 | 0 | 0.06 | 0.04 | 0.02 | 0.22 | 0.04 | 0 | 0.004 | 0.04 |
| 3 | 0.33 | 0.003 | 0.04 | 0.17 | 0.1 | 0.18 | 0.34 | 0.08 | 0 | 0.02 | 0.03 |
| 4 | 0.52 | 0.08 | 0.06 | 0.54 | 0.12 | 0.69 | 0.65 | 0.63 | 0.02 | 0.08 | 0.05 |
| 5 | 1.81 | 0.19 | 0.13 | 0.83 | 0.15 | 1.28 | 1.89 | 0.91 | 0.14 | 0.2 | 0.16 |
| 6 | 2.23 | 1.85 | 1.99 | 1.97 | 0.26 | 2.08 | 2.2 | 2.1 | 0.2 | 0.79 | 0.67 |

E. Formulation Studies

In addition to the above dust control experiments, a number of formulation/hydrotrope studies were conducted in order to develop a higher alkyl glycoside-based system that would be stable at cold temperatures, This work is discussed further in section II, below.

TABLE E

| AG2 - Cold Temperature Stability Tests | |
|---|---|
| Sample/System | Observations (25 hrs at 40° F.) |
| alone: | |
| AG2 at 40% actives | cloudy, crystalline ppt. |
| at 30% actives | " |
| at 20% actives | " |
| for comparison: | |
| AG1 at 50% | clear, no ppt. |
| with salts and urea: | |
| AG2 at 40% actives, plus 5% of: NaCl, CaCl$_2$, Na$_2$SO$_4$, urea with solvents and butyl glucoside: | cloudy crystalline ppt. |

TABLE E-continued

AG2 - Cold Temperature Stability Tests

| Sample/System | Observations (25 hrs at 40° F.) |
|---|---|
| AG2 at 40% actives, plus 10% of: a glycol solvent | cloudy crystalline ppt. |
| lower actives plus additives: | |
| AG2 at 30% actives, plus 6% of: $Na_2SO_4$, urea, Hex. Glyc., EtOH | cloudy with some crystalline solids |
| with sodium cumene sulfonate (SCS) hydrotrope: | |
| AG2 at 40% plus 10% SCS | clear, no ppt. |
| AG2 at 40% plus 6% SCS | clear, no ppt. |
| AG2 at 30% plus 6% SCS | clear, no ppt. |
| AG2 at 30% plus 3% SCS | hazy, some ppt. |
| AG2 at 30% plus 1.5% SCS | cloudy, w/ppt. |
| blends with AG1 (total at 50% actives): | |
| 50/50 AG2/AG1 | clear, no ppt. |
| 67/33 AG2/AG1 | hazy, some ppt. |
| 75/25 AG2/AG1 | cloudy, w/ppt. |
| with extenders: | |
| 10% AG2 plus 25% X9 | cloudy with some ppt. |
| 10% AG2 plus 25% X8 | cloudy with some ppt. |
| 10% AG2 plus 25% X7 | dark, semi-fluid |
| 10% AG2 plus 25% X7 and 6% SCS | clear, dark liquid, no ppt. |

II. Discussion and Results

A. Coal Dust Sinking Time-Wetting

Table A1 shows the results of the coal dust sinking time experiments (described in sect. A) when run in distilled water. The order of efficiency (based on actives, not cost) was:

| most efficient | X5 |
|---|---|
|  | AG2 (very similar to X5) |
|  | AG3 |
|  | AG1 (similar to AG3) |
|  | X1 |
|  | X6 (similar to X1) |
| least efficient | X3 |

Note: In this sinking time experiment, plain water (without surfactant) and non-wetting agents (like X3 and X4) would result in coal dust that would not sink at all, even after standing overnight.

Table A2 show some of these materials also tested in 300 ppm hardness water. They showed the following order of efficiency (on an actives basis):

| most efficient | X6* |
|---|---|
|  | X5* |
|  | AG2 |
|  | X3 |
|  | X1 |
|  | AG3 |
| least efficient | AG1 |

*Efficiency ratings of X6 and X5 reverse depending upon concentration.

In this series, the hard water significantly improved the efficiencies of the sulfosuccinate, and sulfosucciante containing products (i.e., X3 and X1); while the hard water had little impact on the nonionic (i.e., the AG1, AG2 and X5). This changed the orders of efficiencies accordingly.

A few of these surfactants were also evaluated in 2000 ppm hard water. The following efficiencies were noted:

| most efficient | X3 |
|---|---|
|  | X5 |
|  | AG3* |
|  | X1* |
| least efficient | AG2 |

*Ratings cross depending on concentration.

This very hard water improved the efficiency of the X3 further. There was little change (going from 300 to 2000 ppm) for the AG3, mixed results on the X1 product, and a little weaker performance for the AG2 and X5.

B. Coal Dust Rewetting

Table B shows the results of the rewetting experiments described in section I.B. The following orders of efficiency were observed (again on actives, not cost):

| most efficient | X5 |
|---|---|
|  | AG2 (very similar to X5) |
|  | AG3 |
|  | X1 |
|  | X3 |
|  | X6 (very similar to X3) |

These rewetting experiments were done with distilled water only.

C. Hygroscopicity (Moisture Pick-up) of Dried Solids

The results of the moisture experiments (see sect. I.C.) are shown in Table C.

X2 (which is not a wetting agent, Table 2) showed a rapid initial moisture weight gain, but then it dropped off somewhat over time. X7, the blend of AG2 and X7 and AG2 all showed significant hygroscopicity over the time period studies. AG1 and the X3 (see Table 1) were also hygroscopic, but to a lesser extent.

X5 and X1 (Table 2) did not show any moisture gain. The tables actually show a weight loss over time with these materials, but this is probably because the materials were not 100% dry at the start of the test.

D. Blower ("Poofer") Test-Retardation of Drying

Table D shows the retardation of drying effect, using the dust blower (or "poofer") test described in sect. I.D. This test showed the length of time for the treated dust to dry out again and blow around in the test chamber.

The following observations were made regarding effectiveness in this test:

| most effective | blend of AG2 and X7 |
|---|---|
|  | X2 (very similar to the AG2/X7 blend) |
|  | blend of AG2 and X9 |
|  | blend of AG2 and X8 (very similar to the AG2/X9 blend) |
|  | AG2 |
|  | AG3 (very similar to AG2) |
|  | X1 |
|  | X6 (similar to X1) |
|  | X3 |
|  | water only |
| least effective | X4 (very similar to water only) |

X4 (a binder type product) probably did not work well in this experiment because it was applied at too low a concentration. It is normally applied in a high concentration as a coating to form a crush on the dust (see Table 2).

E. Formulation Studies

AG2 was preferred for the dust suppression application, but this material as is (~50% actives in water) separates and forms solids when cooled to about 40° F.

This poses a winter handling problem. Therefore, some formulation experiments were run to develop systems that would be more stable in the cold.

Table E shows the results of these studies. Simply diluting the AG2; or adding salts, urea, or solvents did not solve the problem. However, cold stable systems could be obtained by blending AG1 (50/50) with the AG2, or by adding a sufficient amount of sodium cumene sulfonate (SCS) (about ≧1 part SCS to 7 parts AG2, on solids).

The addition of SCS also allowed the preparation of a cold stable "extended system" with AG2 plus X7 (see Table E).

Note: to assure uniform mixing when diluting to the final working strength, the AG products should be added into water (not an empty tank) with agitation. If agitation is not available, then the AG should be first pre-diluted to less than 10% actives to make them more readily dispersible.

III. Conclusions

Based on our laboratory evaluations, AG2 has been found to be quite useful in products for the suppression and control of industrial, mining, and transportation dust problems. It possesses a unique combination of useful properties for this application. These include:

effective wetting
rapid re-wetting after drying
AG2 solids are hygroscopic (to help keep just moist)
dried AG2 forms a tacky film (can act as a binder)
retarding the drying of wet dust.

The various competitive commercial materials are either wetting agents or binders, but not both.

Further, the alkyl glycosides have the following additional attributes that are useful for this application:

low acute toxicity
low aquatic toxicity
readily biodegradable
low skin and eye irritation These latter properties make them less of a burden in these potentially environmentally intensive dust control applications.

Recommended use levels for coal dust are:
AG2 0.05% actives (in application solution)
AG1 0.1%
AG3 0.1%

EXAMPLE

A dust suppressant composition is prepared by adding from about 0.01% to about 0.10% (solids by weight of the composition) of an alkyl polyglucoside (having (i) an average alkyl size of about 10 carbon atoms and an average D.P. of about 1.5, or (ii) an average alkyl size of about 12.5 carbon atoms and an average D.P. of about 1.8, or (iii) a mixture (typically at 1:1 by weight solids of (i) and (ii)) to environmentally acceptable water (e.g. tap water). From about 0.1% to about 2% (solids by weight of the composition) of a hydrophilic binder material consisting of a methyl glucoside composition available from the Horizon Chemical Division as STA-MEG TM 101 is added to the aqueous composition. The composition is sprayed onto a friable solid (e.g. the surface of a dirt or gravel road) in a substantially dry environment to prevent the generation of dust therefrom during mechanical stress of the friable solid.

What is claimed is:

1. A method of suppressing dust which comprises: contacting a particulate friable solid, in a substantially dry environment, with an aqueous composition which forms a hydroscopic and tacky layer on the particulate friable solid, the composition containing a higher alkyl-glycoside.

2. A method of claim 1 wherein said aqueous composition is comprised of from about 0.001% to about 1% by weight of said higher alkyl glycoside.

3. A method of claim 1 wherein said particulate, friable solid is a mineral.

4. A method of claim 1 wherein said, particulate, friable solid is coal.

5. A method of claim 1 wherein said alkyl glycoside has an alkyl group having an average of at least 8 carbon atoms and an average D.P. of between about 1.2 and about 3.

6. A method of claim 1 further comprising imposing a mechanical stress on said particulate friable solid.

7. A method of claim 1 wherein said aqueous composition is comprised of a hydrophilic binder material.

8. A method of claim 1 wherein the amount of said aqueous composition is insufficient to fluidize said particulating friable solid.

* * * * *